United States Patent
Coffin IV

(10) Patent No.: US 6,943,348 B1
(45) Date of Patent: Sep. 13, 2005

(54) SYSTEM FOR DETECTING INJECTION HOLDING MATERIAL

(75) Inventor: James Price Coffin IV, Trabuco Canyon, CA (US)

(73) Assignee: Masimo Corporation, Irvine, CA (US)

( * ) Notice: Subject to any disclaimer, the term of this patent is extended or adjusted under 35 U.S.C. 154(b) by 769 days.

(21) Appl. No.: 09/422,208

(22) Filed: Oct. 19, 1999

(51) Int. Cl.[7] .............................................. G01N 21/64
(52) U.S. Cl. ..................... 250/302; 250/461.1; 264/408
(58) Field of Search ............................. 250/302, 461.1; 264/408; 252/301.5; 348/130

(56) References Cited

U.S. PATENT DOCUMENTS

| | | | | |
|---|---|---|---|---|
| 4,236,181 A | * | 11/1980 | Shibata et al. ............... | 348/130 |
| 4,632,773 A | * | 12/1986 | Neefe ..................... | 252/301.35 |
| 5,656,210 A | * | 8/1997 | Hill et al. ..................... | 264/2.6 |
| 5,888,424 A | * | 3/1999 | Ebnesajjad et al. ...... | 252/301.5 |
| 6,207,077 B1 | * | 3/2001 | Burnell-Jones ........ | 252/301.36 |

* cited by examiner

*Primary Examiner*—David Porta
*Assistant Examiner*—Shun Lee
(74) *Attorney, Agent, or Firm*—Knobbe, Martens, Olson & Bear, LLP

(57) ABSTRACT

A system is provided for detecting a substantially transparent injection molding material. The injection molding material contains a fluorescent colorant, which is invisible when not exposed to ultraviolet light, but becomes visible when exposed to ultraviolet light. A method of detecting the injection molding material involves exposing the injection molding material to ultraviolet light and examining the material during exposure.

17 Claims, 2 Drawing Sheets

SYSTEM FOR DETECTING INJECTION HOLDING MATERIAL

BACKGROUND OF THE INVENTION

1. Field of the Invention

The present invention relates in general to encapsulation using optically clear compounds, and more particularly to processes such as pour molding, transfer molding, casting, and injection molding.

2. Background

Injection molding is a widely used manufacturing process. In general, the process begins with the injection of a molten stock material, typically a thermoplastic or thermosetting resin, into a mold having several pieces. After the stock material is injected into the mold, it is allowed to cure, and the pieces of the mold are separated to release the product.

The process can be repeated to produce a plurality of instances of the desired product. To repeat the process, the completed product is removed from the mold, and any remaining stock material is removed from the pieces of the mold. The pieces of the mold are then reassembled, and the molten stock material is again injected into the mold.

Occasionally, a transparent stock material is used in an injection molding process. When using a transparent stock material, it can be difficult to detect and remove the remaining stock material when the pieces of the mold are separated at the end of the process. If the pieces of the mold are not fully cleaned before the mold is reused, the remaining stock material can create flaws in subsequent instances of the desired product.

In addition, injection molded products are often inspected for flaws using optical inspection equipment. When the injection molded products are transparent, it can be difficult for the inspection equipment to detect flaws in the products. If the inspection equipment fails to detect a flaw in an injection molded product, then the product may malfunction during use.

SUMMARY OF THE INVENTION

One aspect of the present invention involves a system for detecting a normally transparent injection molding material. According to the present invention, the injection molding material contains a fluorescent colorant, which is invisible when not exposed to ultraviolet light, but becomes visible when exposed to ultraviolet light. The method comprises exposing the injection molding material to ultraviolet light. The system involves an ultraviolet light to expose the colorant.

Another aspect of the present invention involves a method of cleaning an injection molding material from an injection mold and removing the material upon detection. The method involves exposing the mold having injection molding material containing a fluorescent compound to ultraviolet light and removing the material upon detection through the fluorescent colorant.

Another aspect of the present invention involves a method of inspecting a substantially transparent product with an optical instrument, the method comprising incorporating the product with fluorescent colorant and exposing the product to ultraviolet light.

Certain aspects, advantages and features of the present invention are described in the specific embodiment. Not necessarily all such advantages may be achieved in accordance with any particular embodiment of the invention. The invention may be embodied or carried out in a manner that achieves one advantage or group of advantages without necessarily achieving other advantages.

BRIEF DESCRIPTION OF THE DRAWINGS

These and other aspects, advantages, and novel features of the invention are apparent upon reading the following detailed description and upon reference to the accompanying drawings. The present invention is described in more detail below in connection with the attached drawings, in which.

DETAILED DESCRIPTION OF A PREFERRED EMBODIMENT

Figure 1A:
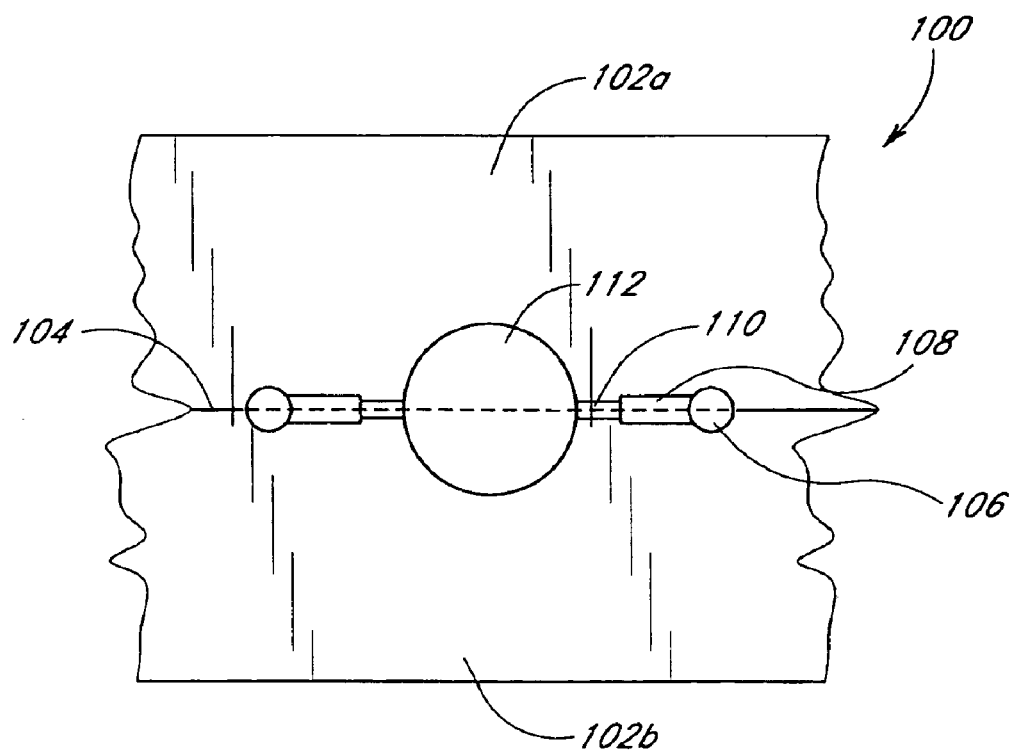
FIG. 1A illustrates a cross-sectional view of an injection mold used in one embodiment of the present invention.

FIG. 1A illustrates a cross-sectional view of an injection mold 100 used in one embodiment of the present invention. The injection mold 100 of the illustrated embodiment comprises an upper piece 102a and a lower piece 102b.

Figure 1B:
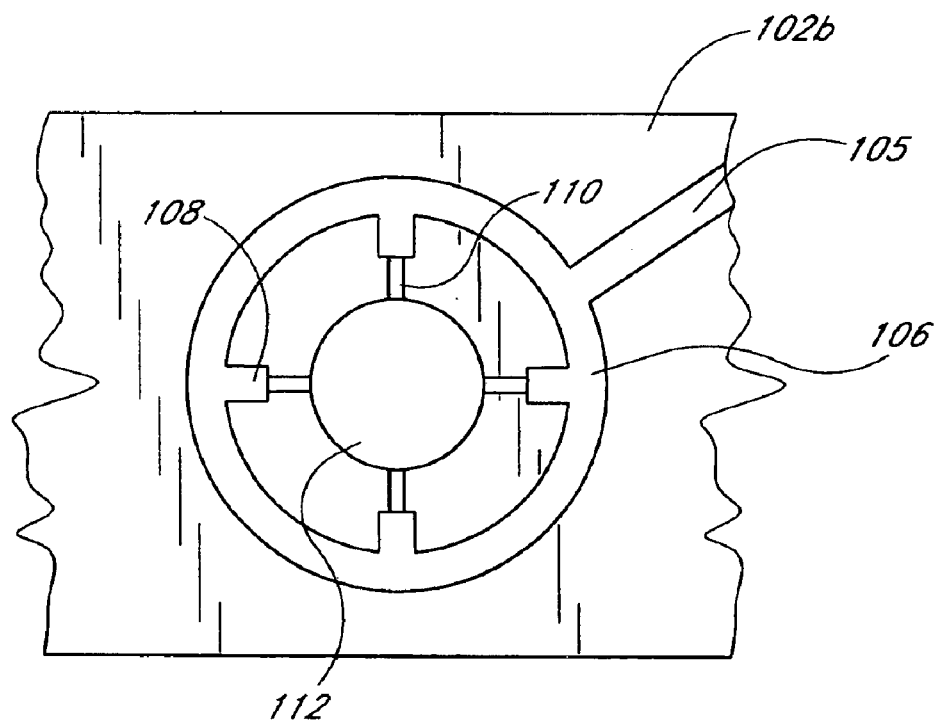
FIG. 1B illustrates a top view of the lower piece of the injection mold illustrated in FIG. 1A.

FIG. 1B illustrates a top view of the lower piece 102b of the injection mold 100. In the illustrated embodiment, the lower piece 102b comprises a plurality of nozzles 108 and a corresponding plurality of gates 110.

When aligned along a separation line 104, the upper and lower pieces 102a and 102b of the injection mold 100 form a main runner 105, an annular runner 106, and a cavity 112. The main runner 105 extends from the outside of the injection mold 100 to the annular runner 106. The annular runner 106 provides an interface between the main runner 105 and the nozzles 108 and corresponding gates 110 of the lower piece 102b. The gates 110 extend from the nozzles 108 into the cavity 112.

In operation, a molten stock material is injected into the main runner 105. The stock material comprises any suitable injection molding material that is substantially transparent. Furthermore, the substantially transparent stock material contains a fluorescent colorant, which is substantially invisible to the eye when not exposed to ultraviolet light, but becomes visible to the eye when exposed to ultraviolet light.

After being injected into the main runner 105, the molten stock material flows into the annular runner 106, where it is distributed to the nozzles 108. The gates 110 are then opened, thereby injecting the molten stock material into the cavity 112. The molten stock material is then allowed to cool. The upper and lower pieces 102a and 102b of the injection mold 100 are then separated to release the desired product.

Figure 2:
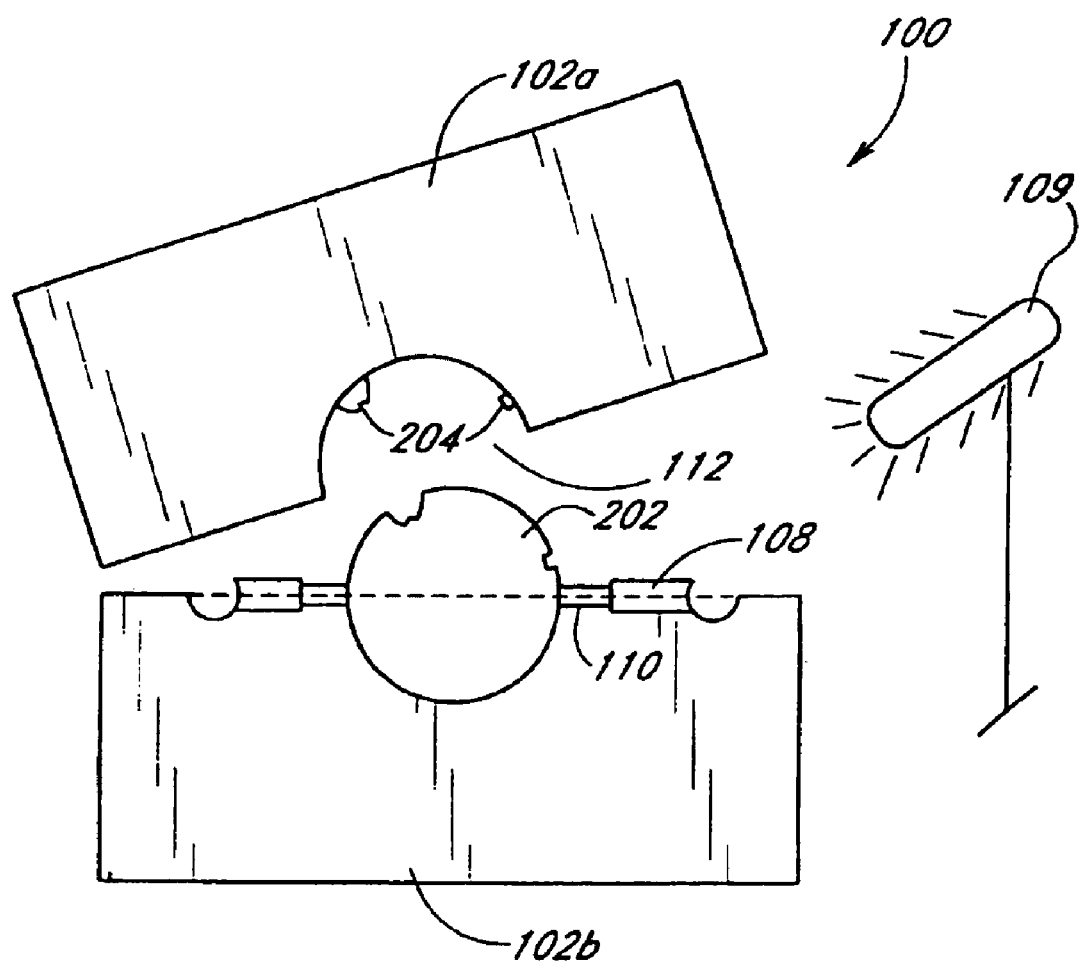
FIG. 2 illustrates a cross-sectional view of the injection mold illustrated in FIG. 1A after use.

FIG. 2 illustrates the injection mold 100 after the upper and lower pieces 102a and 102b have been separated to release the product 202. In the illustrated embodiment, the product 202 comprises a ball. In other embodiments, the product 202 is any product that can be manufactured using any stock material.

After the upper and lower pieces 102a and 102b of the injection mold 100 are separated, the product 202 is removed from the injection mold 100. As illustrated in FIG.

2, remnants 204 of the stock material may remain attached to the injection mold 100 after the product 202 is removed.

Before the injection mold 100 is used again, any remnants 204 of the stock material are removed from the injection mold 100. Because the stock material may be a transparent material, remnants 204 of the stock material can be difficult to detect in the injection mold 100. In the present invention, the upper and lower pieces 102a and 102b of the injection mold 100 are exposed to ultraviolet light, thereby causing the fluorescent colorant in the stock material to become visible to the eye or to automated optical inspection equipment. An ultraviolet light 109 is activated to expose the fluorescent colorant. Accordingly, remnants 204 of the stock material remaining in the injection mold 100 can be detected and removed more easily.

After the remnants 204 of the stock material are removed from the mold 100, the upper and lower pieces 102a and 102b of the mold 100 are realigned and reassembled along separation line 104. The injection molding process may then be repeated to manufacture a plurality of instances of the product 202.

Figure 3:
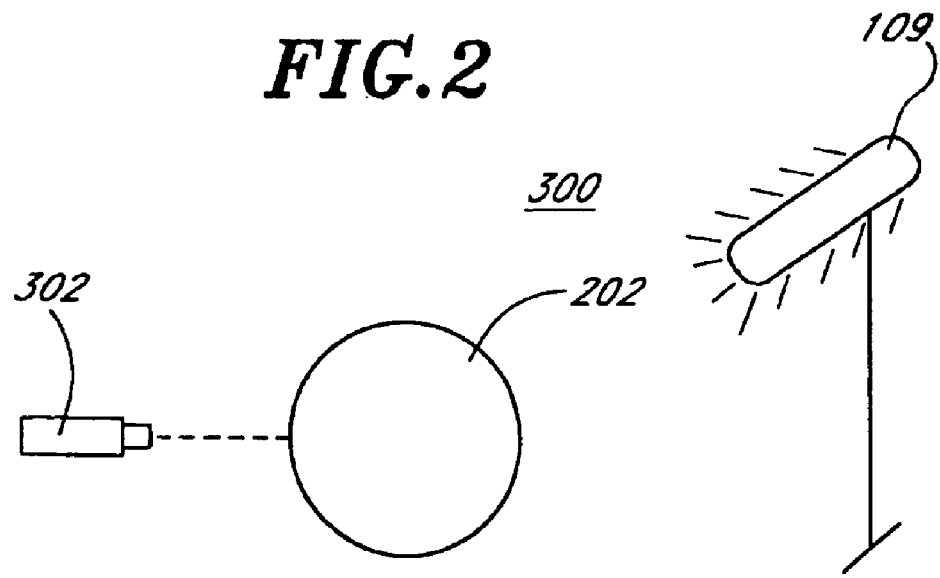
FIG. 3 illustrates a product made in accordance with one embodiment of the present invention undergoing an inspection procedure.

FIG. 3 illustrates a inspection system 300, in accordance with one embodiment of the present invention. The inspection system 300 comprises an inspection device 302 and a product 202. The inspection device 302 may comprise any suitable optical inspection device used to inspect molded products. The product 202 may comprise any suitable product that is can be manufactured using a molding process. The product 202 contains a fluorescent colorant, which is substantially invisible to the inspection device 302 when not exposed to ultraviolet light, but becomes visible to the inspection device 302 when exposed to ultraviolet light.

In use, the inspection device 302 inspects the product 202 for flaws. Such inspection systems are well known in the art. Because the product 202 may be transparent, it can be difficult for the inspection device 302 to detect flaws in the product 202. Therefore, the product 202 is exposed to ultraviolet light while being inspected, thereby causing the fluorescent colorant in the product 202 to become more visible to the inspection device 302. In the present embodiment, the inspection device 302 is configured to be responsive to the fluorescent colorant in the product 202 to perform its inspection operations. Accordingly, the inspection device 302 can detect flaws in the product 202 more easily.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

We claim:

1. A method of determining whether an injection mold is substantially free from any leftover molding material, the method comprising:

injecting molding material including a fluorescent colorant into a mold to create a workpiece;

releasing the mold;

directing ultraviolet light into at least a portion of the mold with sufficient energy to cause emissions from the fluorescent colorant of any remaining molding material to be detectable; and when remaining molding material is detected, removing the remaining molding material.

2. The method of claim 1, wherein the fluorescent colorant is substantially transparent in ambient light.

3. The method of claim 1, wherein the molding material is substantially transparent in ambient light.

4. The method of claim 1, wherein the fluorescent colorant and the molding material are substantially transparent in ambient light.

5. The method of claim 1, wherein the remaining molding material comprises the workpiece.

6. The method of claim 1, wherein the remaining molding material comprises small portions of the workpiece.

7. The method of claim 1, further comprising:

directing the ultraviolet light on the workpiece; and inspecting the workpiece based on a reaction of the workpiece to the ultraviolet light.

8. An optical inspection system for determining whether an injection mold is suitable for reinjection of molding materials, the optical inspection system comprising:

a reusable mold which accepts flowable materials comprising a fluorescent colorant, wherein the flowable materials cool to form a workpiece in the shape of the mold; and a light source which directs ultraviolet light toward the reusable mold with sufficient energy to energize the fluorescent colorant of any leftover flowable materials within the reusable mold.

9. The optical inspection system of claim 8, wherein the fluorescent colorant is substantially transparent in ambient light.

10. The optical inspection system of claim 8, wherein the flowable materials are substantially transparent in ambient light.

11. The optical inspection system of claim 8, wherein the flowable materials and the fluorescent colorant are substantially transparent in ambient light.

12. The optical inspection system of claim 8, wherein the leftover flowable materials comprise the workpiece.

13. The optical inspection system of claim 8, wherein the leftover flowable materials comprise small portions of the workpiece.

14. An optical inspection system for determining whether flaws or other abnormalities occurred in a workpiece made from an injection molding process, the optical inspection system comprising:

a light source which directs a first light toward a workpiece made from materials including a fluorescent colorant, wherein the first light comprises light of a wavelength not visible to humans with sufficient energy to cause the fluorescent colorant to emit a second light;

an inspection device which inspects the workpiece by detecting the second light, wherein the second light comprises light of a wavelength visible to humans.

15. The optical inspection system of claim 14, wherein the fluorescent colorant is substantially transparent in ambient light.

16. The optical inspection system of claim 14, wherein the materials are substantially transparent in ambient light.

17. The optical inspection system of claim 14, wherein the materials and the fluorescent colorant are substantially transparent in ambient light.

* * * * *

UNITED STATES PATENT AND TRADEMARK OFFICE
CERTIFICATE OF CORRECTION

PATENT NO. : 6,943,348 B1  Page 1 of 1
APPLICATION NO. : 09/422208
DATED : September 13, 2005
INVENTOR(S) : James Price Coffin It is certified that error appears in the above-identified patent and that said Letters Patent is hereby corrected as shown below:

In Title Page, item 54, Column 1 (Title), Line 2, please delete "HOLDING" and insert -- MOLDING --, therefore.

Column 1, Line 2, please delete "HOLDING" and insert -- MOLDING --, therefore.

Column 3, Line 23, please delete "a" and insert -- an --, therefore.

Signed and Sealed this

Tenth Day of July, 2007

JON W. DUDAS
*Director of the United States Patent and Trademark Office*